US011278669B2

(12) United States Patent
Dowd et al.

(10) Patent No.: US 11,278,669 B2
(45) Date of Patent: Mar. 22, 2022

(54) GEAR-DRIVEN INFUSION ASSEMBLIES, SYSTEMS, AND METHODS

(71) Applicant: Repro Med Systems, Inc., Chester, NY (US)

(72) Inventors: Paul Dowd, Scarsdale, NY (US); Jessica Grace Huffman, Wilton, CT (US)

(73) Assignee: Repro Med Systems, Inc., Chester, NY (US)

( * ) Notice: Subject to any disclaimer, the term of this patent is extended or adjusted under 35 U.S.C. 154(b) by 200 days.

(21) Appl. No.: 16/747,581

(22) Filed: Jan. 21, 2020

(65) Prior Publication Data

US 2021/0220551 A1 Jul. 22, 2021

(51) Int. Cl.
*A61M 5/145* (2006.01)
*A61M 5/315* (2006.01)
*A61M 5/48* (2006.01)
*A61M 5/142* (2006.01)

(52) U.S. Cl.
CPC ...... *A61M 5/1454* (2013.01); *A61M 5/31586* (2013.01); *A61M 5/482* (2013.01); *A61M 5/1424* (2013.01); *A61M 5/31558* (2013.01); *A61M 5/31575* (2013.01); *A61M 2005/14506* (2013.01); *A61M 2005/14533* (2013.01); *A61M 2005/3152* (2013.01)

(58) Field of Classification Search
CPC ............ A61M 5/1454; A61M 5/31586; A61M 5/482; A61M 5/31558; A61M 5/31575; A61M 2005/3152; A61M 5/1424; A61M 2005/14506; A61M 2005/14533; A61M 5/14566
See application file for complete search history.

(56) References Cited

U.S. PATENT DOCUMENTS

| 4,059,110 A | 11/1977 | Wuthrich et al. |
|---|---|---|
| 4,253,464 A | 3/1981 | Zorgniotti et al. |
| 4,300,554 A | 11/1981 | Hessberg et al. |
| 4,447,232 A | 5/1984 | Sealfon et al. |
| 4,557,728 A | 12/1985 | Sealfon et al. |

(Continued)

OTHER PUBLICATIONS

International Search Report and Written Opinion dated May 25, 2021 in related International Patent Application No. PCT/US21/13534.

*Primary Examiner* — Nilay J Shah

(74) *Attorney, Agent, or Firm* — Eric L. Lane; Green Patent Law

(57) ABSTRACT

A gear-driven infusion assembly is provided which has a housing, a gear assembly coupled to the housing, a shuttle assembly slidably coupled to the housing and operably coupled to the gear assembly, and a tube enclosure connected to the housing. The tube enclosure is configured to house a primary drug closure such as a syringe. The gear assembly includes a spool assembly having a pinion gear and a drive spool. When the spring rotates the drive spool, the drive spool drives the pinion gear, and the gear assembly drives the shuttle assembly. When the gear assembly drives the shuttle assembly, the shuttle assembly slides longitudinally along the housing. The gear assembly may be spring driven such that a spring rotates the pinion gear about the drive spool. An overspeed protection device is also provided which has a spool assembly including a drive spool.

19 Claims, 14 Drawing Sheets

(56) References Cited

U.S. PATENT DOCUMENTS

| | | | |
|---|---|---|---|
| 4,602,700 A * | 7/1986 | Szabo | A61M 5/1454 185/38 |
| 4,604,994 A | 8/1986 | Sealfon | |
| 4,676,122 A * | 6/1987 | Szabo | A61M 5/1454 74/625 |
| 4,921,487 A | 5/1990 | Buffet et al. | |
| 6,575,946 B2 | 6/2003 | Sealfon | |
| 6,926,706 B1 | 8/2005 | Sealfon | |
| D714,931 S | 10/2014 | Sealfon | |
| 10,376,636 B2 | 8/2019 | Sealfon | |
| 10,406,282 B2 | 9/2019 | Sealfon et al. | |
| 2015/0126926 A1 * | 5/2015 | Giambattista | A61M 5/1454 604/135 |
| 2015/0374911 A1 | 12/2015 | Sealfon | |
| 2016/0067424 A1 | 3/2016 | Sealfon et al. | |
| 2016/0213284 A1 | 7/2016 | Sealfon | |
| 2016/0250422 A1 * | 9/2016 | Koch | A61M 5/14248 604/110 |
| 2016/0256625 A1 | 9/2016 | Sealfon et al. | |
| 2016/0339226 A1 | 11/2016 | Sealfon | |
| 2017/0087295 A1 | 3/2017 | Sealfon et al. | |
| 2017/0165415 A1 | 6/2017 | Sealfon et al. | |
| 2017/0189666 A1 | 7/2017 | Sealfon et al. | |
| 2018/0099086 A1 | 4/2018 | Sealfon et al. | |
| 2018/0099101 A1 | 4/2018 | Sealfon et al. | |
| 2018/0116909 A1 | 5/2018 | Sealfon et al. | |
| 2019/0201620 A1 | 7/2019 | Sealfon et al. | |
| 2020/0009330 A1 | 1/2020 | Sealfon et al. | |
| 2020/0069930 A1 | 3/2020 | Sealfon et al. | |

* cited by examiner

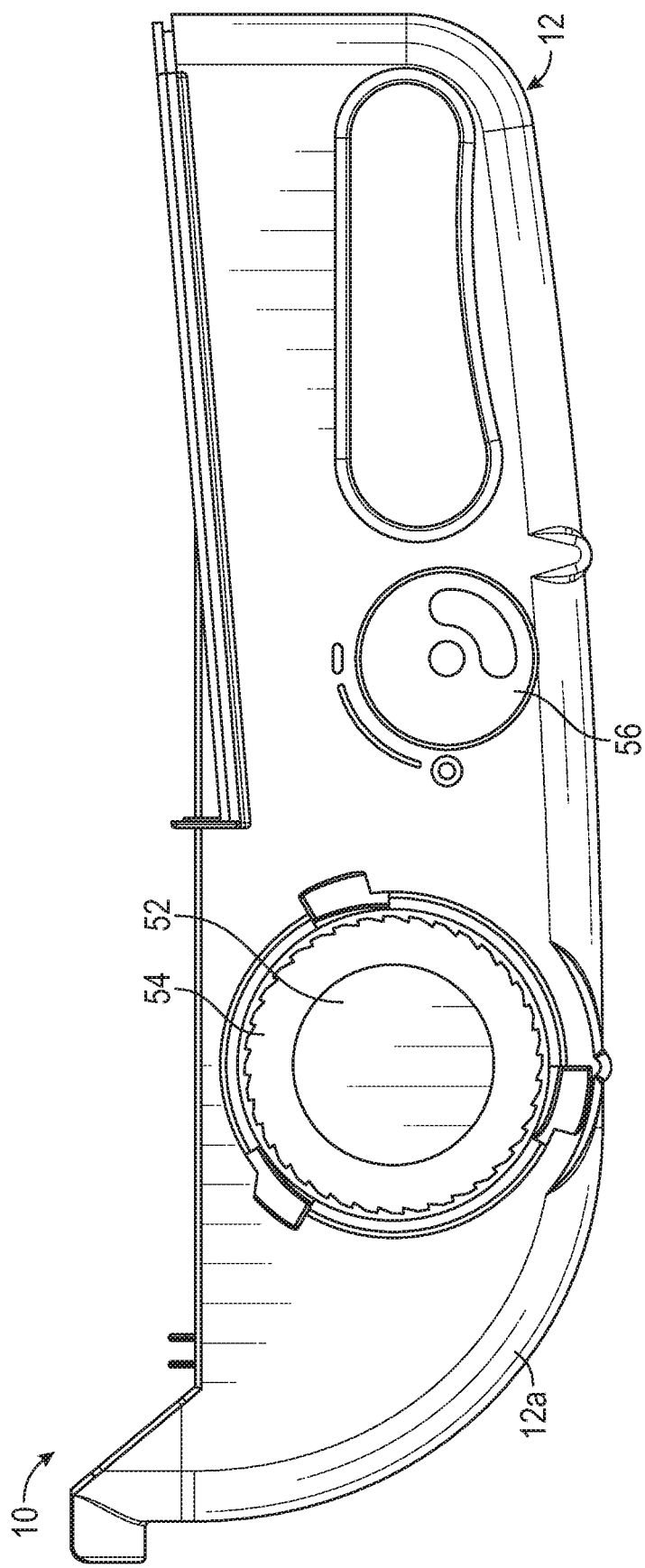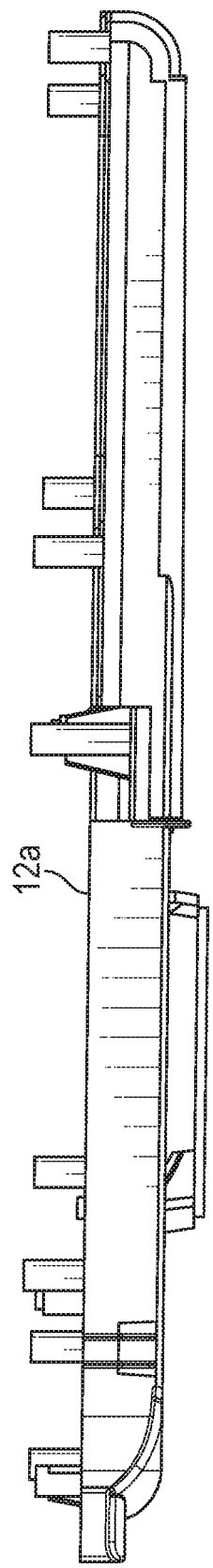
FIG. 1A
FIG. 1B

GEAR-DRIVEN INFUSION ASSEMBLIES, SYSTEMS, AND METHODS

FIELD OF THE DISCLOSURE

This application relates to infusion assemblies, systems, and methods. This application further relates to gear-driven infusion assemblies used with primary drug closures.

BACKGROUND

A variety of medical conditions require individuals to receive regular infusions of medicaments. However, infusions typically occur slowly over a period of time and may need to be administered by a medical professional. Thus, an individual may need to travel regularly to a medical facility to receive needed infusions and spend a lot of time at such a facility on each visit.

Infusion devices have been developed that allow individuals to administer infusions of needed medicaments. Infusion devices commonly used for such purposes may incorporate a system of one or more cables and pulleys to regulate the flow of the medicament and provide tensioning and overspeed protection. This type of mechanism can provide a mechanical advantage and transmit the force of a spring to a shuttle, which pushes on a primary drug closure. However, assembly of such cable and pulley mechanisms can be time-consuming and expensive, and the cable can occasionally get tangled.

Accordingly, there is a need for an infusion device that can be manufactured more efficiently. There is also a need for an infusion device with improved flow regulation and tensioning mechanisms. There is a need for an improved infusion device that provides flow regulation, tensioning, and overspeed protection without the need for a cable and pully system.

SUMMARY

The present disclosure, in its many embodiments, alleviates to a great extent the disadvantages of known infusion devices, assemblies, and methods by providing a gear-driven infusion assembly. Disclosed embodiments differ from current infusion systems in at least two significant areas, i.e., driving the shuttle and sensing the load on the system. The present disclosure describes a gear-driven and, in some embodiments, spring-driven infusion system where a gear drives a rack or shuttle, which pushes on a primary drug closure. This system of gears is more straightforward and more robust than a cable and pulley system. A torque sensor or torque-activated mechanical actuator is provided for the purpose of disengaging a slowdown gear train in a syringe pump or for disengaging a slowdown device in other applications. Disclosed gear-driven infusion assemblies advantageously provide a great deal of force as well as control and safety.

Exemplary embodiments of a gear-driven infusion assembly comprise a housing, a retainer plate coupled to the housing, a gear assembly coupled to the housing and the retainer plate, a shuttle assembly slidably coupled to the housing and operably coupled to the gear assembly, and a tube enclosure connected to the housing. The tube enclosure is configured to house a primary drug closure. The housing may comprise a top housing piece and a bottom housing piece. In exemplary embodiments, the infusion assembly further comprises a compound gear operably coupled to the gear assembly and an idler gear operably coupled to the compound gear. The gear assembly comprises a spool assembly including a pinion gear, a spring, and a drive spool. The shuttle assembly may include a shuttle, a gear rack, and a claw piece.

When the spring rotates the drive spool, the drive spool drives the pinion gear, and the gear assembly drives the shuttle assembly, so the shuttle assembly slides longitudinally along the housing. In exemplary embodiments, a primary drug closure is operably coupled to the shuttle assembly. When the shuttle assembly slides, it exerts a force on an end of the primary drug closure. The force exerted on the end of the primary drug closure pushes fluid out of the primary drug closure. In exemplary embodiments, the primary drug closure is a syringe.

In exemplary embodiments, the spool assembly provides overspeed protection. The pinion gear may have a plurality of spiral cam surfaces around its perimeter, and the drive spool may have a plurality of cams that mate with the spiral cam surfaces. In exemplary embodiments, the pinion gear is not directly connected to the drive spool and is coaxially rotatable with the drive spool through a limited angle of rotation. When a load on the gear assembly is below a threshold level the pinion gear remains in place, and when a load on the gear assembly rises above a threshold level the pinion gear rotates relative to the drive spool.

Exemplary embodiments of a gear-driven infusion assembly comprise a housing, a gear assembly coupled to the housing, and a shuttle assembly slidably coupled to the housing and operably coupled to the gear assembly. The gear assembly may comprise a spool assembly including a pinion gear and a drive spool. When the drive spool drives the pinion gear, the gear assembly drives the shuttle assembly, thereby sliding the shuttle assembly longitudinally along the housing. In exemplary embodiments, a tube enclosure is provided, and a primary drug closure is at least partially disposed in the tube enclosure and operably coupled to the shuttle assembly. When the shuttle assembly slides, it exerts a force on an end of the primary drug closure. That force pushes fluid out of the primary drug closure. In exemplary embodiments, the primary drug closure is a syringe.

In exemplary embodiments, the gear assembly further comprises a spring, and the spring biases the pinion gear in a rotational direction by applying a moment to the pinion relative to the main spool. The pinion gear may have a plurality of spiral cam surfaces around its perimeter, and the drive spool may have a plurality of cams that mate with the spiral cam surfaces. In exemplary embodiments, the pinion gear is not directly connected to the drive spool and is coaxially rotatable with the drive spool through a limited angle of rotation. When a load on the gear assembly is below a threshold level the pinion gear remains in place, and when a load on the gear assembly rises above a threshold level the pinion gear rotates relative to the drive spool. In exemplary embodiments, the infusion assembly has a compound gear operably coupled to the gear assembly and an idler gear operably coupled to the compound gear. The infusion assembly may further comprise a retainer plate coupled to the housing and the gear assembly.

Exemplary embodiments of an overspeed protection device are disclosed herein, comprising a spool assembly including a drive spool having a plurality of cams, a spring, and a pinion gear. The pinion gear is coaxially rotatable with the drive spool through a limited angle of rotation but not directly connected to the drive spool, and the pinion gear has a plurality of spiral cam surfaces around its perimeter that mate with the cams. When a load on the spool assembly is below a threshold level the pinion gear remains in place, and when a load on the spool assembly rises above a threshold level the pinion gear rotates relative to the drive spool. In exemplary embodiments, the spring biases the pinion gear against one end of the limited angle of rotation. The overspeed protection device may be used in various applications, including with a primary drug closure.

Accordingly, it is seen that gear-driven infusion assemblies, systems, and methods are provided. These and other features and advantages will be appreciated from review of the following detailed description, along with the accompanying figures in which like reference numbers refer to like parts throughout.

BRIEF DESCRIPTION OF THE DRAWINGS

The above-mentioned features and objects of the present disclosure will become more apparent with reference to the following description taken in conjunction with the accompanying drawings wherein like reference numerals denote like elements and in which:

FIG. 1A is a top view of an exemplary embodiment of a gear-driven infusion assembly in accordance with the present disclosure;

FIG. 1B is a front view of an exemplary embodiment of a top housing piece of a gear-driven infusion assembly in accordance with the present disclosure;

DETAILED DESCRIPTION

Figure 1C:
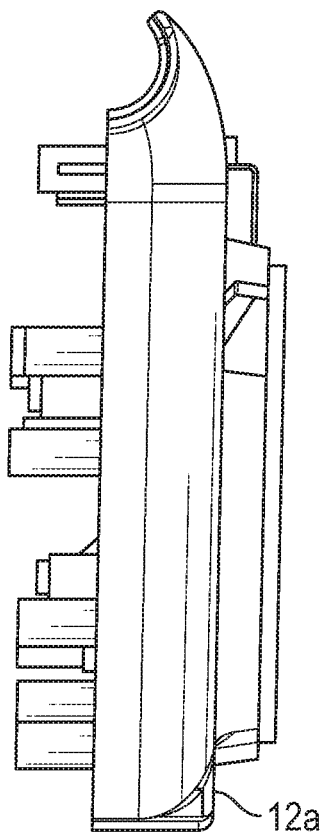
FIG. 1C is a side view of an exemplary embodiment of a top housing piece of a gear-driven infusion assembly in accordance with the present disclosure.
Figure 1D:
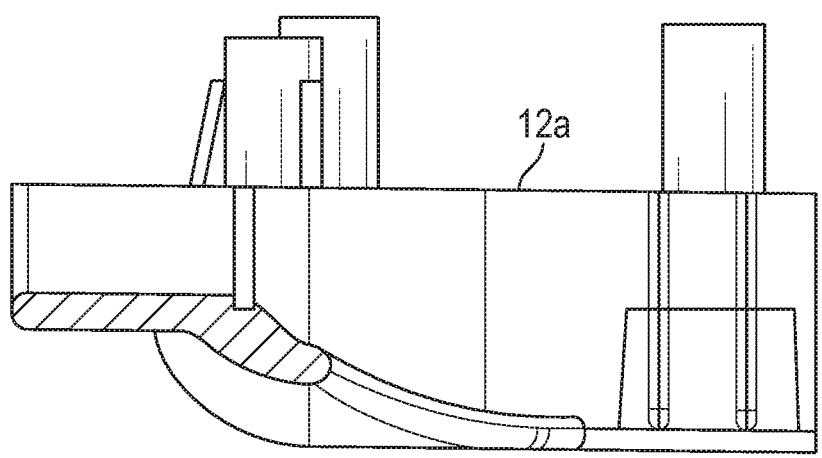
FIG. 1D is a detail view of an exemplary embodiment of a top housing piece of a gear-driven infusion assembly in accordance with the present disclosure.
Figure 1G:
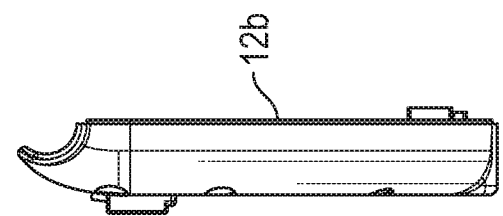
FIG. 1G is a side view of an exemplary embodiment of a bottom housing piece of a gear-driven infusion assembly in accordance with the present disclosure.
Figure 1H:
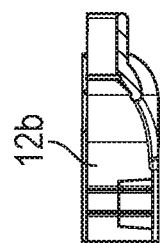
FIG. 1H is a detail view of an exemplary embodiment of a bottom housing piece of a gear-driven infusion assembly in accordance with the present disclosure
Figure 1E:
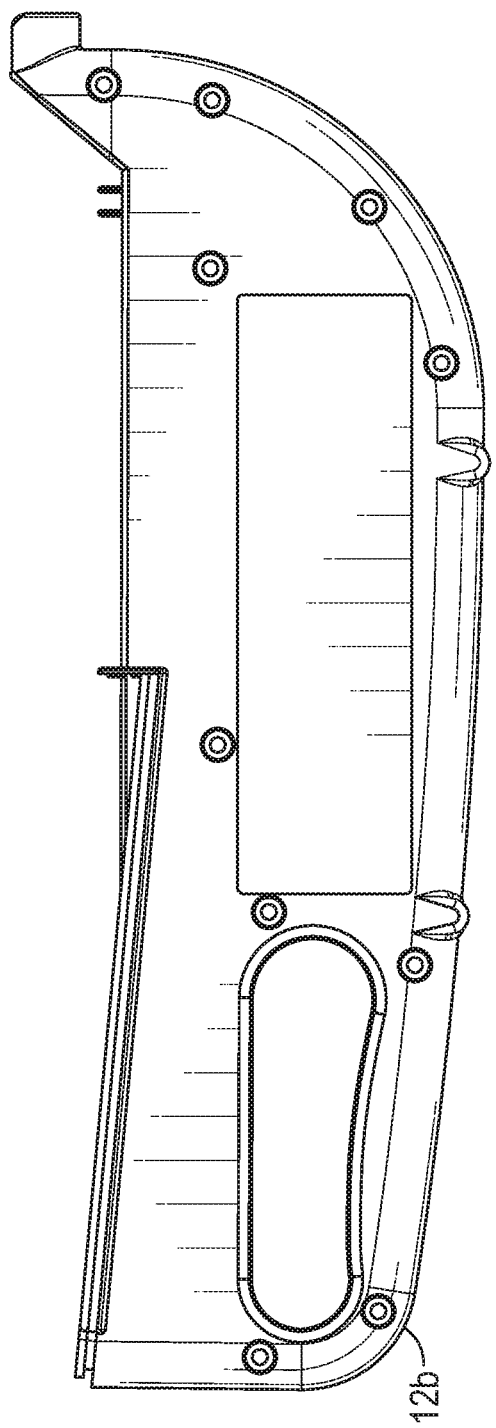
FIG. 1E is a top view of an exemplary embodiment of a bottom housing piece of a gear-driven infusion assembly in accordance with the present disclosure.
Figure 1F:
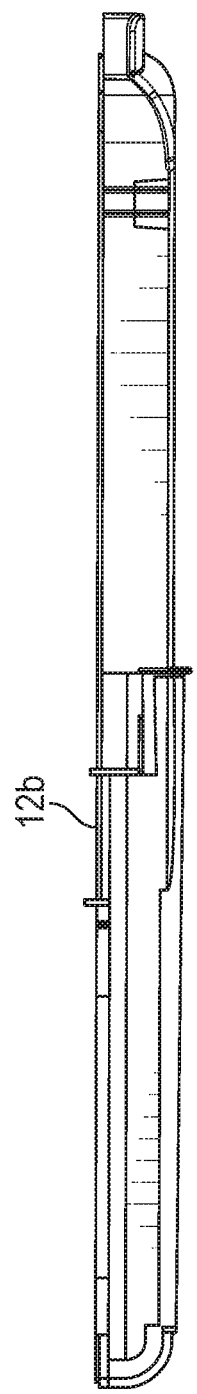
FIG. 1F is a front view of an exemplary embodiment of a bottom housing piece of a gear-driven infusion assembly in accordance with the present disclosure.

In the following detailed description of exemplary embodiments of the disclosure, reference is made to the accompanying drawings in which like references indicate similar elements, and in which is shown by way of illustration specific embodiments in which disclosed systems and devices may be practiced. These embodiments are described in sufficient detail to enable those skilled in the art to practice the embodiments, and it is to be understood that other embodiments may be utilized, and that logical, mechanical, functional, and other changes may be made without departing from the scope of the present disclosure. The following detailed description is, therefore, not to be taken in a limiting sense, and the scope of the present disclosure is defined by the appended claims. As used in the present disclosure, the term "or" shall be understood to be defined as a logical disjunction and shall not indicate an exclusive disjunction.

FIGS. 1A-1H, 2A and 2B illustrate an exemplary embodiment of a gear-driven infusion assembly 10. Housing 12 contains most of the operable components of the assembly 10. The housing 12 could be a one-piece component or have two or more pieces such as a top housing piece 12a and a bottom housing piece 12b that are connected to form the full housing. In exemplary embodiments, a retainer plate 14 is coupled to the housing 12 to provide an additional structural surface for attachment of the gear assembly 16 and other components as needed. Retainer plate 14 may be connected to both the top housing piece 12a and the bottom housing piece 12b.

A gear assembly 16 is located between retainer plate 14 and top housing piece 12a and includes multiple components. Gear assembly 16 is coupled to the retainer plate 14 and top housing piece 12a via one or more of these components. As discussed in more detail herein, gear assembly 16 serves to drive a shuttle assembly 38, which acts on a primary closure device to push fluid out of the primary closure device. In addition, parts of the gear assembly provide tensioning and overspeed protection. The gear assembly 16 includes a spool assembly 18 comprised of a drive spool 20 and a pinion gear 22.

Figure 3:
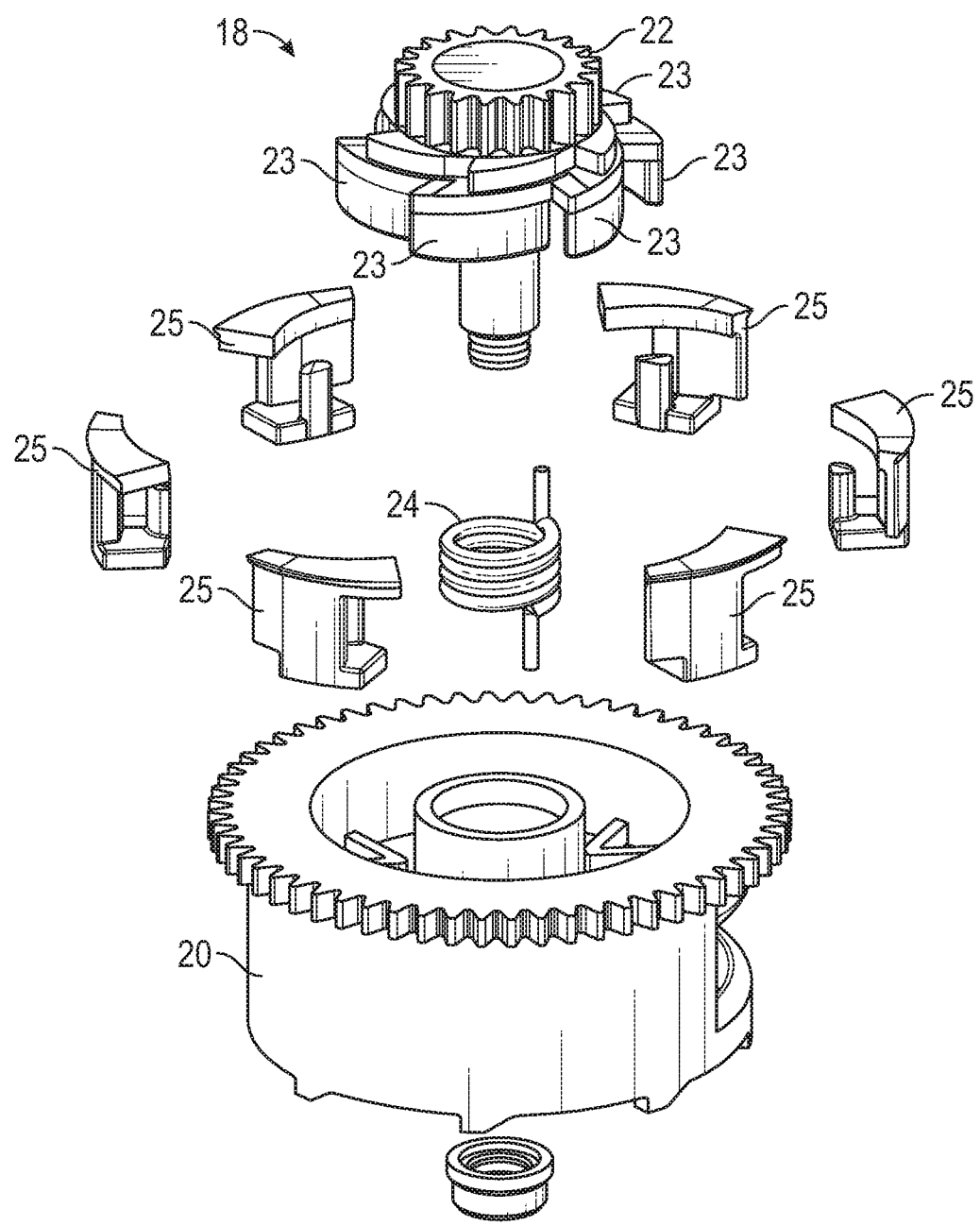
FIG. 3 is an exploded view of a spool assembly or overspeed protection device in accordance with the present disclosure.

In exemplary embodiments, as best seen in FIG. 3, the pinion gear 22 has spiral cam surfaces 23 around its perimeter, and the drive spool 20 may have cams 25 that mate with the spiral cam surfaces 23. As discussed in more detail herein, during operation this system of spiral cam surfaces 23 and corresponding cams 25 senses the load or torsion on the infusion assembly and may force main spool cams 25 outward, resulting in their outer edges approximating a larger diameter circle. In exemplary embodiments, the gear assembly 16 utilizes spring force, and the spool assembly 18 includes a spring 24. As discussed in more detail herein, the spring force acts indirectly on the pinion gear 22 through drive spool 20, and the pinion gear amplifies the force of the spring 24. The source of amplification is the difference in diameter between the outer surface of spool 20 and the pitch diameter of pinion gear 22. Pinion gear 22 is not directly connected to drive spool 20 and is therefore able to rotate coaxially with the drive spool 20 through a limited angle of rotation.

Figure 10:
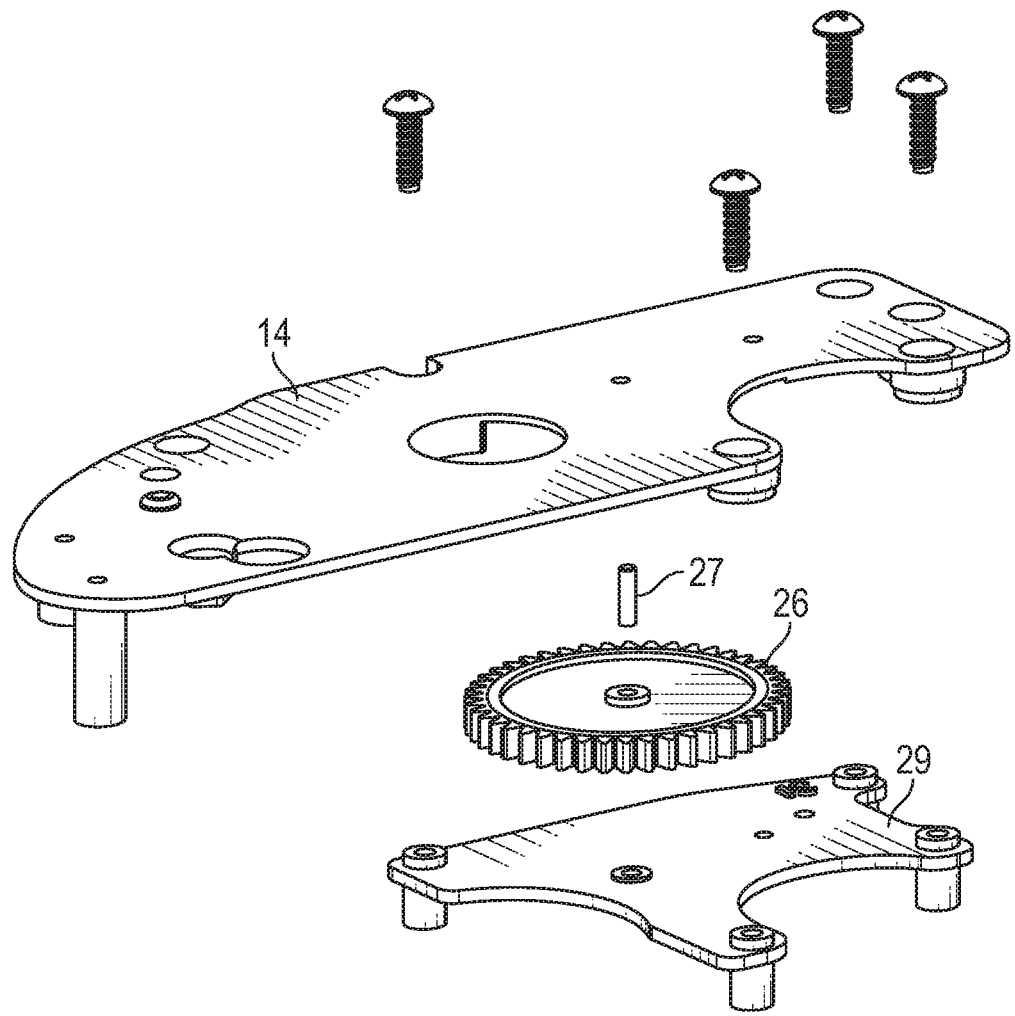
FIG. 10 is an exploded view of an exemplary embodiment of an idler gear in accordance with the present disclosure.

Additional gears and related components may be utilized as part of gear assembly 16 or in conjunction with it on the drive side and slowdown side of the gear assembly. For example, on the drive side idler gear 26 with a pivot spring 28 may be connected to retainer plate 14 below it and operably connected to a drive compound gear 36 above it. Also, the drive spool 20 is in operable communication with the idler gear 26 via pinion gear 22 and drives the idler gear. The components accompanying an exemplary idler gear 26 and idler gear system including an idler pin 27 and inner assembly plate 29 are illustrated in FIG. 10. The teeth of the drive compound gear 36 are in operational contact with the teeth of the shuttle 39 so rotation of the drive compound gear 36 drives the shuttle assembly 38. On the slowdown side, gear assembly 16 may include a brake gear 32 and brake shoe 34 to limit rotation of the drive spool 20. As discussed in more detail herein, the slowdown side components act as a speed regulation system governor to slow down the shuttle assembly 38.

In exemplary embodiments, shuttle assembly 38 is disposed in a portion of housing 12 specially sized and shaped for the shuttle. When top and bottom housing pieces 12a, 12b are connected and closed together the shuttle assembly 38 is coupled to the housing 12 such that it can slide back and forth longitudinally. In exemplary embodiments, shuttle assembly 38 is operably coupled to drive compound gear 36. The teeth of drive compound gear 36 are in operational contact with the teeth of the drive spool 20. As discussed in more detail herein, rotation of the gear assembly 16 causes rotation of the drive compound gear 36, which acts to slide the shuttle assembly 38.

Figure 2A:
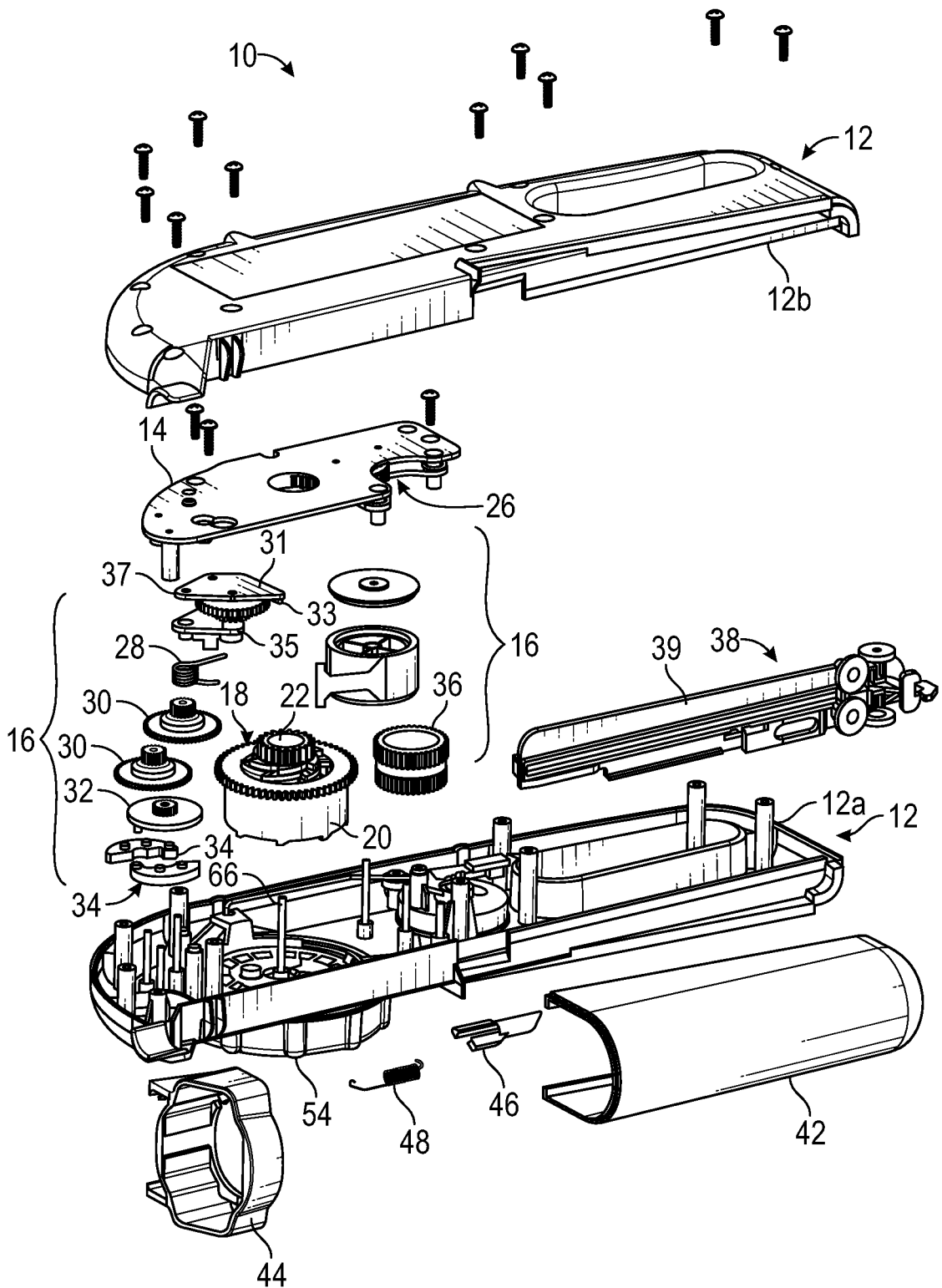
FIG. 2A is an exploded view of an exemplary embodiment of a gear-driven infusion assembly in accordance with the present disclosure.
Figure 4:
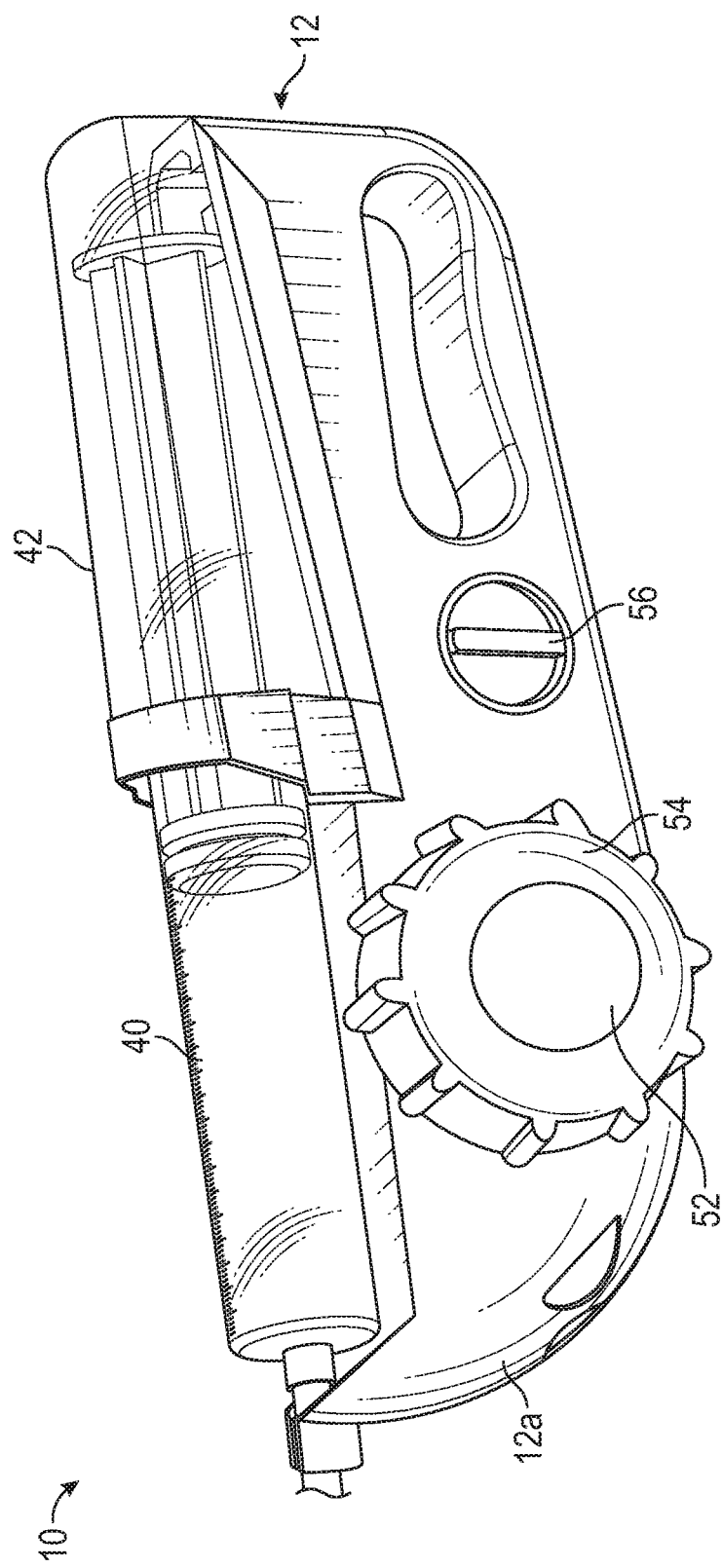
FIG. 4 is a perspective view of an exemplary embodiment of a gear-driven infusion assembly in accordance with the present disclosure.
Figure 5:
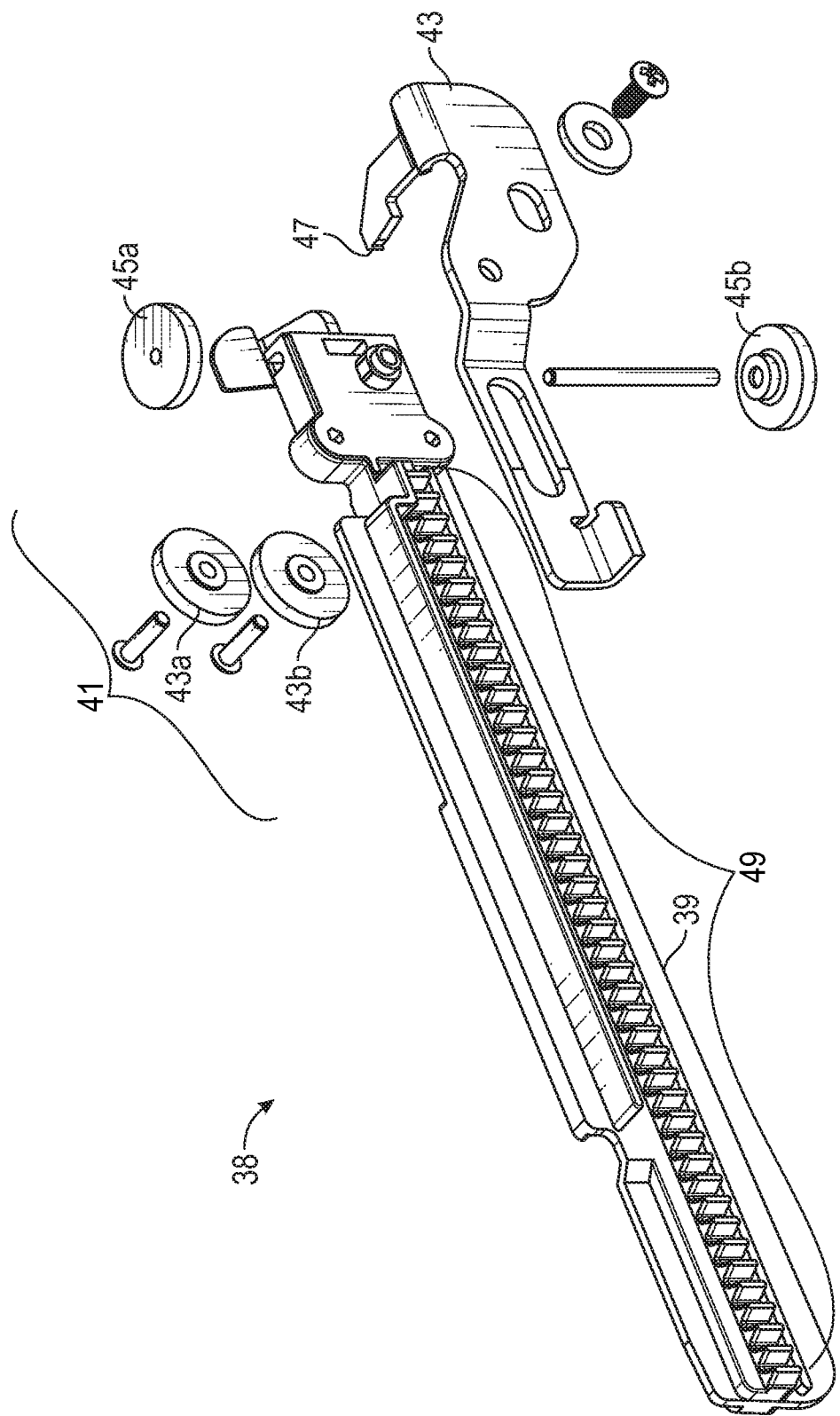
FIG. 5 is an exploded view of an exemplary embodiment of a shuttle assembly in accordance with the present disclosure.
Figure 6D:
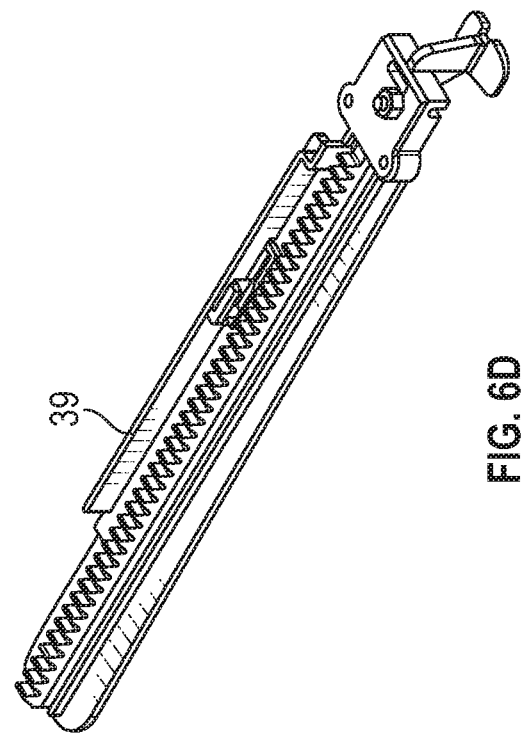
FIG. 6D is a perspective view of an exemplary embodiment of a shuttle assembly in accordance with the present disclosure.
Figure 6A:
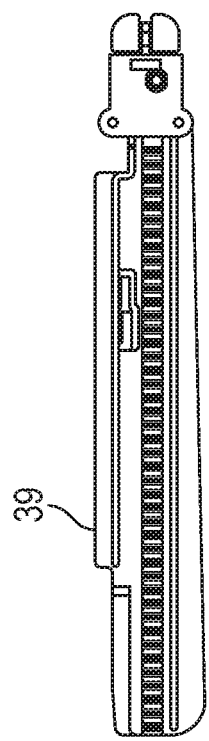
FIG. 6A is a side view of an exemplary embodiment of a shuttle assembly in accordance with the present disclosure.
Figure 6B:
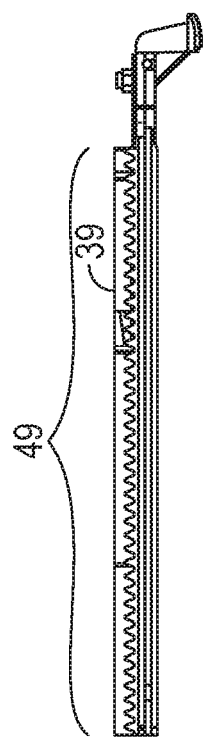
FIG. 6B is a top view of an exemplary embodiment of a shuttle assembly in accordance with the present disclosure.
Figure 6C:
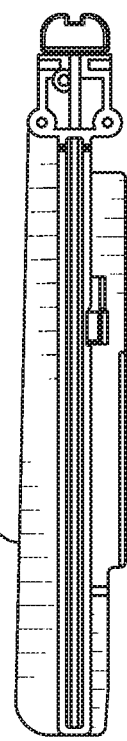
FIG. 6C is a side view of an exemplary embodiment of a shuttle assembly in accordance with the present disclosure.
Figure 7:
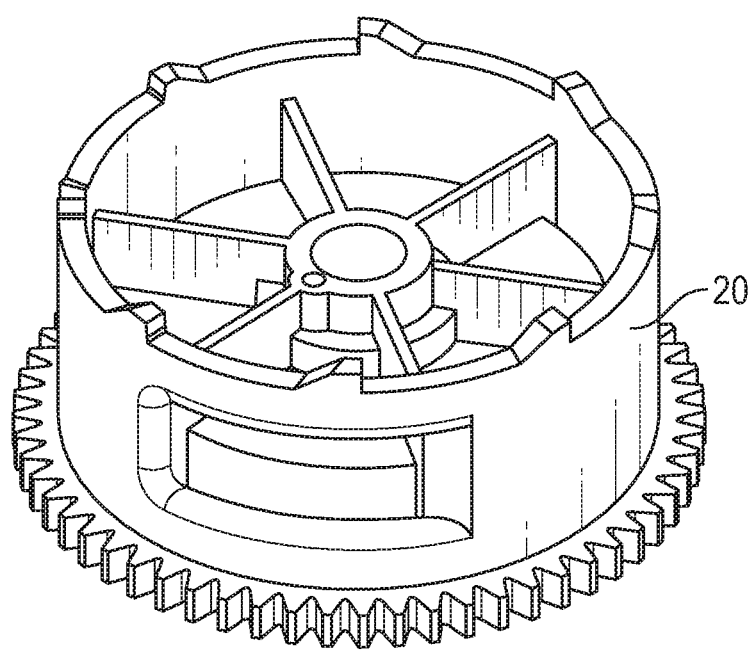
FIG. 7 is a perspective view of an exemplary embodiment of a main spool in accordance with the present disclosure.
Figure 8C:
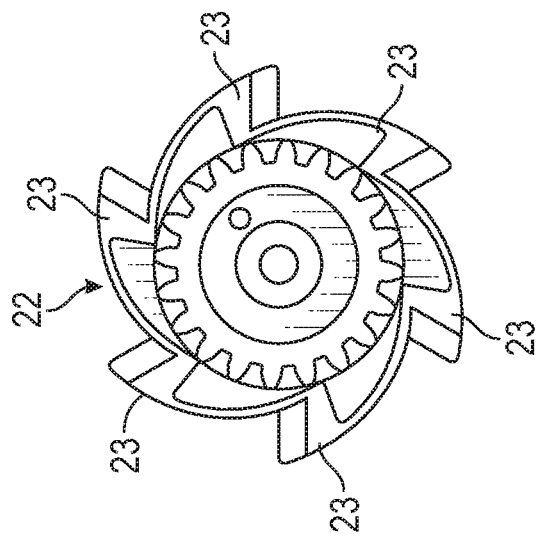
FIG. 8C is a top view of an exemplary embodiment of a pinion gear with spiral cam surfaces in accordance with the present disclosure.
Figure 8B:
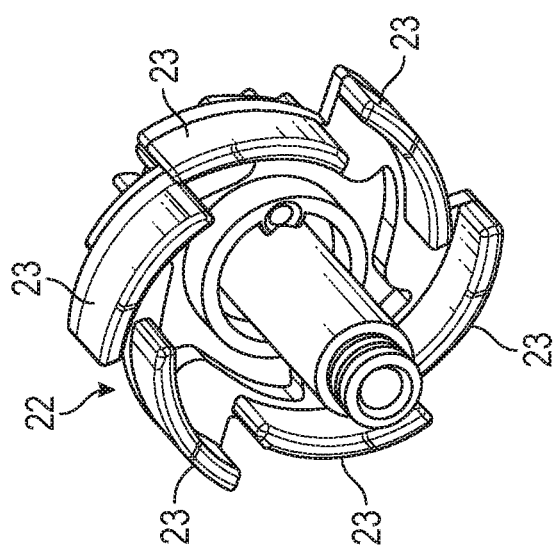
FIG. 8B is a rear perspective view of an exemplary embodiment of a pinion gear with spiral cam surfaces in accordance with the present disclosure.
Figure 8D:
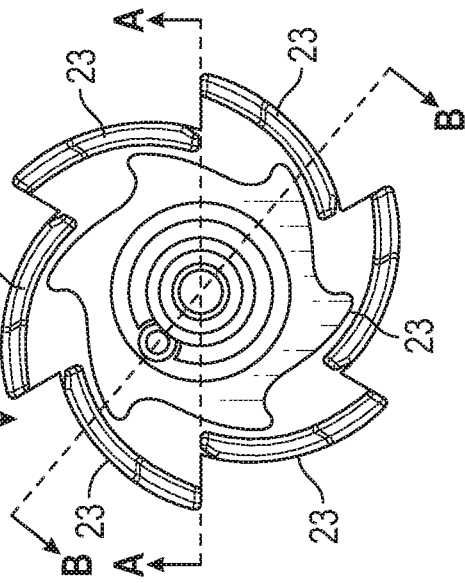
FIG. 8D is a bottom view of an exemplary embodiment of a pinion gear with spiral cam surfaces in accordance with the present disclosure.
Figure 8A:
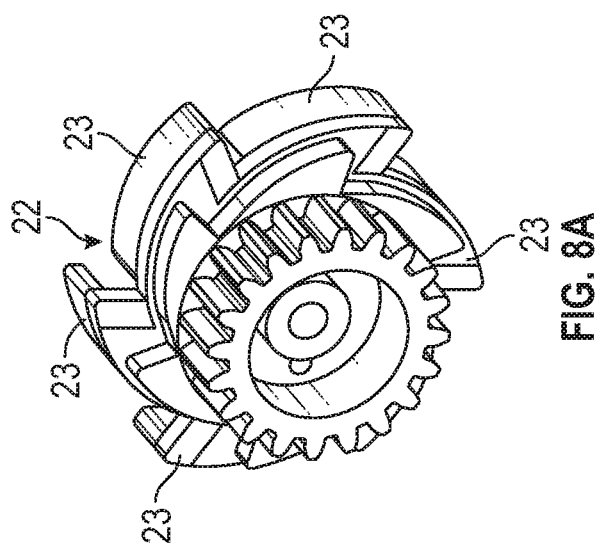
FIG. 8A is a front perspective view of an exemplary embodiment of a pinion gear with spiral cam surfaces in accordance with the present disclosure.
Figure 9A:
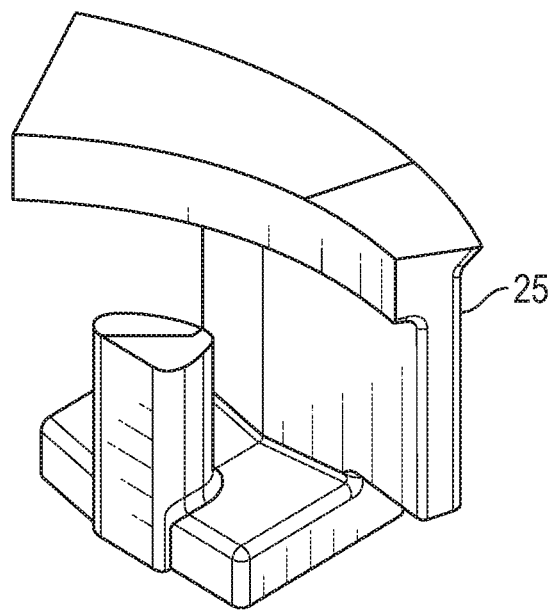
FIG. 9A is a perspective view of an exemplary embodiment of a cam in accordance with the present disclosure.
Figure 9B:
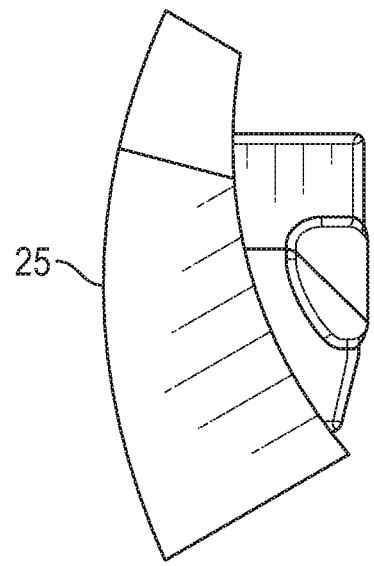
FIG. 9B is a top view of an exemplary embodiment of a cam in accordance with the present disclosure.
Figure 9C:
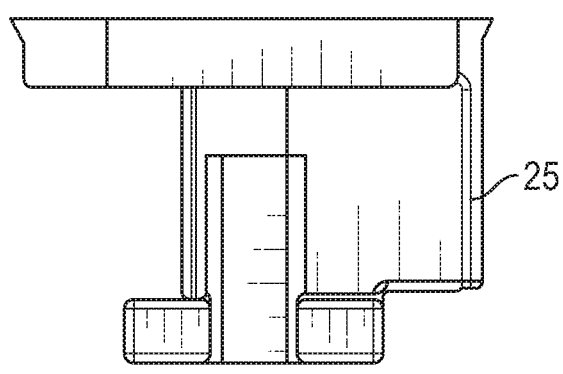
FIG. 9C is a front view of an exemplary embodiment of a cam in accordance with the present disclosure.
Figure 9D:
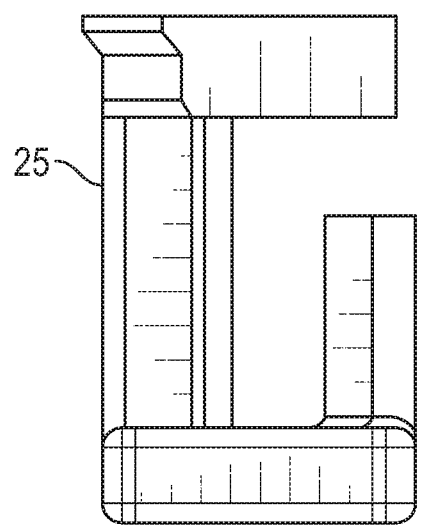
FIG. 9D is a side view of an exemplary embodiment of a cam in accordance with the present disclosure.

With reference to FIGS. 2A and 4, gear-driven infusion assembly 10 is designed so a primary drug closure 40 can be coupled to it to supply medicament to a user. The primary drug closure 40 can be connected to the shuttle assembly 38. In exemplary embodiments, the primary drug closure 40 is a syringe. More particularly, a tube enclosure 42, also called a primary drug closure shield or syringe shield, is connected to housing 12, and the syringe 40 is disposed within the tube enclosure 42. A tube cap 44 may be provided, and the front of the syringe 40 extends into the cap 44. In exemplary embodiments, a syringe locator 46 and syringe spring 48 serve to assist insertion and/or operation of the syringe 40. When the syringe 40 is disposed within the syringe shield 42 and fully coupled to the infusion assembly 10, the shuttle assembly 38 is positioned so that when it slides forward it exerts a force on the end of the syringe 40, thereby pushing medicament out of the syringe.

Turning to FIGS. 5 and 6A-6D, an exemplary shuttle assembly will now be described. The main components of shuttle assembly 38 are shuttle 39, gear rack 41, and claw piece 43. In exemplary embodiments, the gear rack 41 is integrally molded into the shuttle assembly 38. The gear rack 41 has several wheels and a series of teeth 49, and in exemplary embodiments the wheels include two vertically oriented wheels 43a, 43b and two horizontally oriented wheels 45a, 45b. These two pairs of wheels help to maintain the shuttle 39 in its operable position so it slides in a longitudinal direction along the housing without moving up or down or side to side. The horizontal wheels 45a, 45b prevent up and down movement of the shuttle in the directions of the top and bottom housing pieces 12a, 12b and rotation about the longitudinal axis of the gear rack 41, and the vertical wheels prevent side to side movement, along with a ball bearing (not shown) in the housing 12. In exemplary embodiments, the claw piece 43 attaches to a distal end of the shuttle 39, with the left half and right half connecting on opposite sides of the shuttle 39 such that the claw piece extends across the end of the shuttle. A sharp point 47 on claw piece 43 may be provided to dig into the end of a syringe plunger so the syringe plunger doesn't slip or move out of position.

Figure 2B:
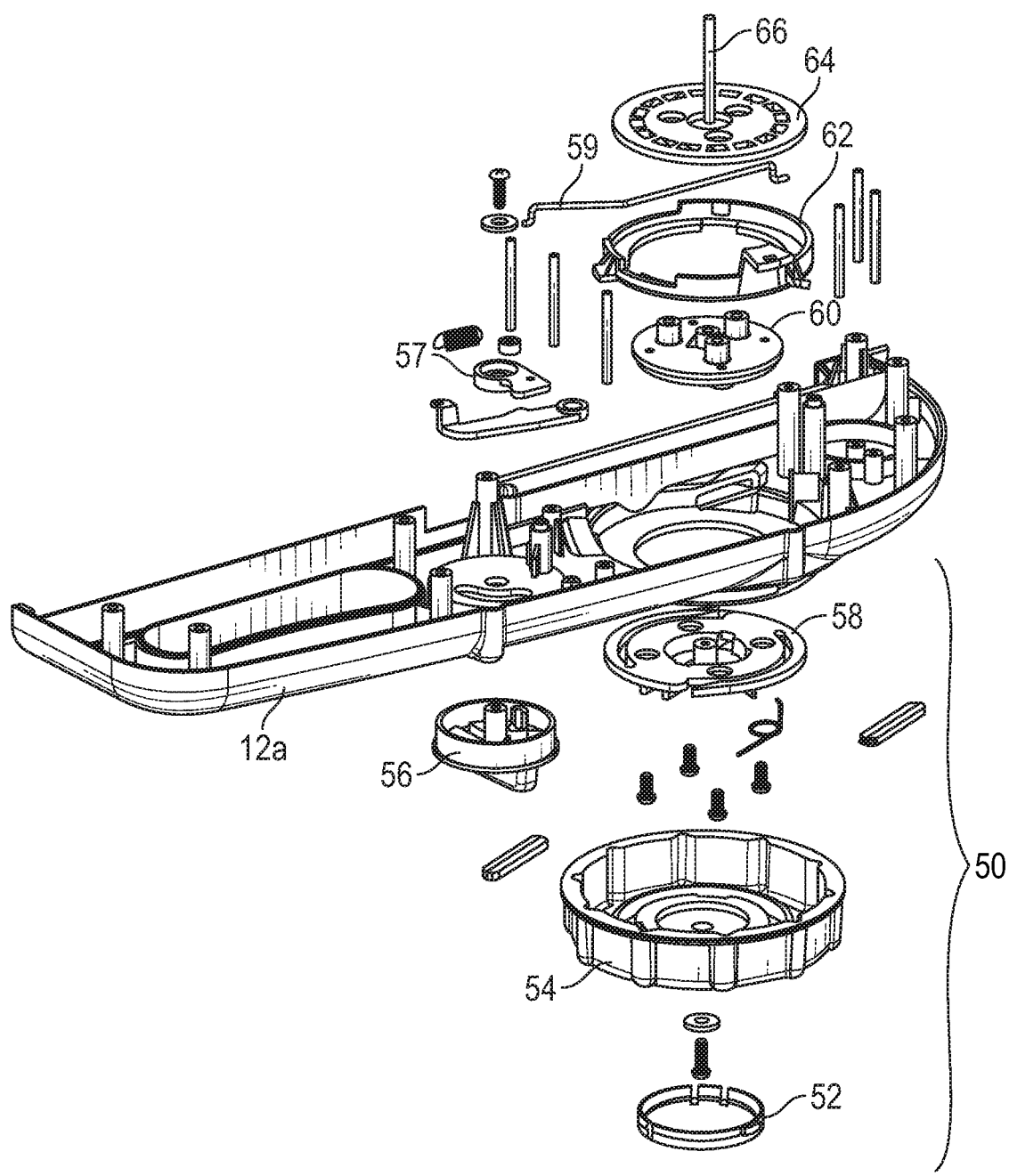
FIG. 2B is an exploded view of an exemplary embodiment of a top housing piece of a gear-driven infusion assembly in accordance with the present disclosure.

As best seen in FIG. 2B, a knob and switch assembly 50 is incorporated into top housing piece 12a and provides a mechanism for the user to control the infusion assembly 10. A knob cap 52 is coupled to knob 54, both of which extend out from the perimeter of the housing 12 for easy access so a user can wind the knob. A series of components, including but not limited to, switch 56, switch plate 57 and linkage 59, ratchet 58, dog plate 60, iris 62, and dog 64 may be provided. One of skill in the art would be able to vary or substitute these components as needed. These components are connected in series, culminating in the main spool shaft 66 on which spool assembly 18 is mounted to provide operable communication from the user's manipulation of the knob 54 to the gear assembly 16.

Returning to FIG. 3, and referring to FIGS. 7, 8A-8D and 9A-9D, spool assembly 18, which serves as an overspeed protection device, will now be described in more detail. An exemplary overspeed protection device or spool assembly 18 is comprised of a main drive spool 20, a main spool spring 24, a plurality of main spool cams 25, and drive pinion or pinion gear 22. Main spool spring 24 is located about the shaft of the pinion gear 22, which is disposed in the center of the main drive spool 20. Pinion gear 22 amplifies the force of the main spool spring 24. In exemplary embodiments, pinion gear 22 is not directly connected to the main drive spool 20. As such, the pinion gear 22 is free to rotate coaxially with the main drive spool 20 through a limited angle of rotation. The main spool spring 24 biases the pinion gear 22 against one end of that limited angle travel.

As best seen in FIG. 3, overspeed protection device or spool assembly 18 incorporates a twist-actuated cam design for tensioning and overspeed protection. More particularly, pinion gear 22 has a plurality of spiral cam surfaces 23 around its perimeter. In addition, main drive spool 20 has a plurality of main spool cams 25 of approximately corresponding shape to the spiral cam surfaces 23 such that they can partially mate with them as the spool assembly 18 rotates. This design senses the load or torsion on the infusion assembly and moves the main spool cams 25 outward, resulting in their outer edges approximating a larger diameter circle of the main drive spool 20 as the spool assembly 18 twists. More generally, the purpose of this design is to ensure that the slowdown gear train is disconnected during an infusion and connected all other times in order to protect the infusion assembly 10 from overspeed.

In operation, a user who needs to perform an infusion of a medicament would connect a syringe 40 or other suitable primary drug closure to the gear-driven infusion assembly 10 by inserting the syringe within the syringe shield 42. In exemplary embodiments, the user positions the syringe 40 so the front of the syringe 40 extends into tube cap 44. Thus installed, the syringe 40 is positioned so that it is in operational contact with shuttle assembly 38. The user then turns switch 56, which activates the spool assembly 18 by acting on iris 62, which in turn moves dog 64 away from drive spool 20. This disengages the teeth on the drive spool 20 from the slots in the dog 64, thus freeing the spring 24 to act through the spool.

When spool assembly 18 is activated, it begins to rotate. More particularly, the force of spring 24 acts on pinion gear 22, which amplifies the force of the spring. In exemplary embodiments, the pinion gear 22 amplifies the force of the spring 24 by about 3½ times, since the spring operates at a diameter of about 1¾ inches, which is the OD of the drive spool 20. Thus, spring 24 rotates the drive spool 20 about the spool shaft. To get the driving force from the pinion gear 22 to the shuttle assembly 38, idler gear 26 and compound gear 36 operate in sequence to drive the gear assembly 16 and operate the shuttle assembly 38.

When the operational force is transmitted from spool assembly 18 through compound gear 36, the gear assembly 16 drives the shuttle assembly 38. As best seen in FIG. 2A, compound gear 36 has two sets of teeth. When the spool assembly 18 rotates, the teeth of pinion gear 22 and drive spool 20 each engage a respective set of teeth on the compound gear 36. The teeth of the drive compound gear 36 also are in operational contact with the teeth of the shuttle 39 so rotation of the drive compound gear 36 engages and drives the shuttle assembly 38. The teeth of the drive compound gear 36 are in operational contact with the teeth of the shuttle 39 so the rotation of the drive compound gear 36 engages the shuttle assembly 38.

The shuttle assembly 38 accepts the load from the drive compound gear 36, and the claw piece 43 provides the output of the shuttle assembly. The load from the drive side of the gear assembly 16 causes the shuttle assembly 38 to slide forward longitudinally in the infusion assembly 10. Because an end of the shuttle assembly 38 is engaged with an end of the syringe 40, this sliding movement of the shuttle assembly exerts force on the syringe and pushes the medicament out of the syringe. In exemplary embodiments, the claw piece 43 engages with the end of the syringe 40 and pushes the plunger. The sharp point 47 on claw piece 43 digs into the end of a syringe so the syringe doesn't slip or move out of position during administration of the medicament.

Exemplary methods of overspeed protection will now be described. Overspeed protection may occur, for example, in instances where the syringe is not loaded. The load on the infusion assembly 10 needs to be sensed in order to start the slowdown side function. When the infusion assembly 10 is operated without a syringe, the user will hear a distinctive noise, which is the spinning of the gears and speed brake associated with this regulation system. Once the infusion starts, there is a "click" and then silence. That click is caused by the load sensor forcing the slowdown side out of engagement with the spool assembly 18.

Figure 11:
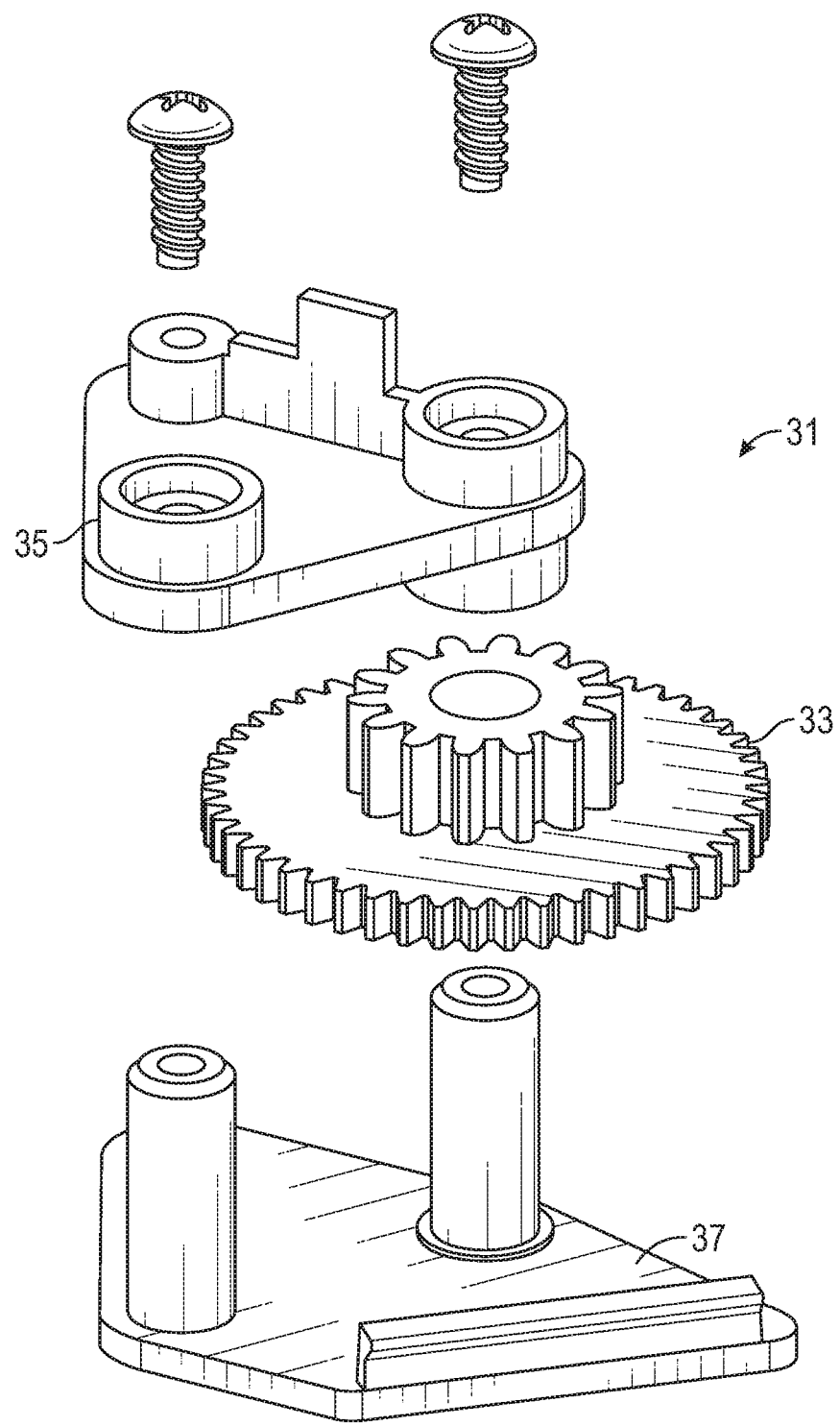
FIG. 11 is an exploded view of an exemplary embodiment of a swing gear in accordance with the present disclosure.

As discussed above, the twist-actuated cam design of spool assembly 18 provides tensioning and overspeed protection, sensing the load or torsion on the infusion assembly and moving main spool cams 25 of the spool assembly 18 outward, resulting in their outer edges approximating a larger virtual diameter as the spool assembly 18 twists. Generally, when there is no load on the spool assembly 18 or the load is below a threshold level, the pinion gear 22 remains in place, which allows the biasing spring 24 to rotate the pinion gear 22 relative to the drive spool 20, thereby retracting the circular array of cam followers into their smallest diameter configuration. When the load on the spool assembly 18 rises above a threshold level, which is determined by the spring 24, the pinion gear 22 rotates relative to the drive spool 20 against the force of the biasing spring 24, thereby extending the circular array of main spool cams 25 into their largest diameter configuration. In this larger diameter state, the main spool cams 25 displace the swing gear assembly 31, forcing the swing gear 33 to rotate about the axis of gear 30 against the moment of pivot spring 28 thereby disconnecting swing gear 33 from the main spool. As illustrated in FIG. 11, in exemplary embodiments, swing gear assembly 31 is comprised of swing gear 33, actuator arm 37, and plate 35.

In operation, the medicament or air in the syringe 40 applies resistance, or the syringe may include a resistance feature. The slowdown side of the gear assembly 16 creates resistance on the drive spool assembly 18 via brake gear 32 and brake shoe 34, and the resistance is amplified by gear 30 and swing gear 33. In exemplary embodiments, the spring 24 spins brake gear 32, which causes brake shoe 34 to fling out and rub on the housing 12, acting as a speed-sensitive brake, as a governor or centripetal brake would. Brake gear 32 engages slowdown compound gears 30, which engage swing gear 33 and engages the spur in the slowdown compound gears. This causes the spring 24 to disengage, and the ultimate effect is to slow down the shuttle assembly 38.

Accordingly, the force or tension being delivered by the gears from the resistance of the syringe is sensed by the overspeed protection device or spool assembly 18. This sensing is achieved because, as discussed above, the pinion gear 22 on the drive spool 20 is not directly connected to the drive spool. Rather, it is free to rotate coaxially with the drive spool 20 through a limited angle of rotation. In addition, spring 24 biases pinion gear 22 against one end of that limited angle travel. The spiral cam surfaces 23 on the pinion gear 22, almost like spiraled starfish legs, are arrayed around its perimeter. These cam surfaces 23 act on an array of cam followers or main spool cams 25 whose outer edges collectively approximate a circle. The main spool cams 25 are restricted to move in a radial direction by slots in the drive spool 20. As the starfish-shaped pinion gear 22 rotates relative to the drive spool 20, the cam surfaces 23 force the main spool cams 25 outward, resulting in their outer edges approximating a larger diameter circle. This, now larger, outer circular edge pushes an actuator arm 37, which in turn pushes the arm that locates the swing gear 33 in the speed regulator, disengaging it.

Thus, it is seen that improved infusion assemblies, systems, and methods are provided. It should be understood that any of the foregoing configurations and specialized components may be interchangeably used with any of the systems of the preceding embodiments. Although illustrative embodiments are described hereinabove, it will be evident to one skilled in the art that various changes and modifications may be made therein without departing from the disclosure. It is intended in the appended claims to cover all such changes and modifications that fall within the true spirit and scope of the disclosure.

While the disclosed systems and devices have been described in terms of what are presently considered to be the most practical exemplary embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

The invention claimed is:

1. A gear-driven infusion assembly, comprising:
a housing;
a retainer plate coupled to the housing;
a gear assembly coupled to the housing and the retainer plate, the gear assembly comprising a spool assembly including a pinion gear, a spring, and a drive spool;
a shuttle assembly slidably coupled to the housing and operably coupled to the gear assembly; and
a tube enclosure connected to the housing, the tube enclosure being configured to house a primary drug closure;
wherein when the spring rotates the drive spool, the drive spool drives the pinion gear, and the gear assembly drives the shuttle assembly;
wherein when the gear assembly drives the shuttle assembly, the shuttle assembly slides longitudinally along the housing; and
wherein the spool assembly provides overspeed protection by changing diameter.

2. The gear-driven infusion assembly of claim 1 wherein the primary drug closure is disposed at least partially within the tube enclosure and operably coupled to the shuttle assembly;
wherein when the shuttle assembly slides the shuttle assembly exerts a force on an end of the primary drug closure and pushes fluid out of the primary drug closure.

3. The gear-driven infusion assembly of claim 2 wherein the primary drug closure is a syringe.

4. The gear-driven infusion assembly of claim 1 wherein the pinion gear has a plurality of spiral cam surfaces around the pinion gear perimeter and the drive spool has a plurality of cams that mate with the spiral cam surfaces.

5. The gear-driven infusion assembly of claim 1 wherein the pinion gear is not directly connected to the drive spool and is coaxially rotatable with the drive spool through a limited angle of rotation.

6. The gear-driven infusion assembly of claim 5 wherein when a load on the gear assembly is below a threshold level the pinion gear remains in place, and when the load on the gear assembly rises above the threshold level the pinion gear rotates relative to the drive spool.

7. The gear-driven infusion assembly of claim 1 wherein the housing comprises a top housing piece and a bottom housing piece.

8. The gear-driven infusion assembly of claim 1 further comprising a compound gear operably coupled to the gear assembly.

9. The gear-driven infusion assembly of claim 1 wherein the shuttle assembly comprises a shuttle and a claw piece.

10. A gear-driven infusion assembly, comprising:
a housing;
a gear assembly coupled to the housing, the gear assembly comprising a spool assembly including a pinion gear and a drive spool; and
a shuttle assembly slidably coupled to the housing and operably coupled to the gear assembly;
wherein when the drive spool drives the pinion gear, the gear assembly drives the shuttle assembly;
wherein when the gear assembly drives the shuttle assembly, the shuttle assembly slides longitudinally along the housing; and
wherein the spool assembly provides overspeed protection by changing diameter.

11. The gear-driven infusion assembly of claim 10 wherein the gear assembly further comprises a spring, the spring biasing the pinion gear in a rotational direction.

12. The gear-driven infusion assembly of claim 10 further comprising a retainer plate coupled to the housing and the gear assembly.

13. The gear-driven infusion assembly of claim 10 further comprising a tube enclosure connected to the housing and a primary drug closure at least partially disposed within the tube enclosure and operably coupled to the shuttle assembly.

14. The gear-driven infusion assembly of claim 10 wherein the pinion gear has a plurality of spiral cam surfaces around the pinion gear perimeter and the drive spool has a plurality of cams that mate with the spiral cam surfaces.

15. The gear-driven infusion assembly of claim 14 wherein the pinion gear is not directly connected to the drive spool and is coaxially rotatable with the drive spool through a limited angle of rotation;
wherein when a load on the gear assembly is below the threshold level the pinion gear remains in place, and when the load on the gear assembly rises above a threshold value the pinion gear rotates relative to the drive spool.

16. The gear-driven infusion assembly of claim 10 further comprising a compound gear operably coupled to the gear assembly.

17. An overspeed protection device comprising:
a spool assembly including:
a drive spool having a plurality of cams, each cam having an outer edge;
a spring; and
a pinion gear, the pinion gear being coaxially rotatable with the drive spool through a limited angle of rotation but not directly connected to the drive spool, the pinion gear having a plurality of spiral cam surfaces around the pinion gear perimeter that mate with the cams;
wherein when a load on the spool assembly is below a threshold level the pinion gear remains in place, and when the load on the spool assembly rises above the threshold level the pinion gear rotates relative to the drive spool and extends the cams outward such that the outer edges of the cams have a larger diameter configuration.

18. The device of claim 17 wherein the spring biases the pinion gear against one end of the limited angle of rotation.

19. A gear-driven infusion assembly comprising the overspeed protection device of claim 17, wherein the gear-driven infusion assembly further comprises:
a housing containing the overspeed protection device;
a gear assembly;
a retainer plate coupled to the overspeed protection device;

a shuttle assembly slidably coupled to the housing and operably coupled to the gear assembly; and a primary drug closure housed within the shuttle assembly.

\* \* \* \* \*